(12) United States Patent
Bailly et al.

(10) Patent No.: US 8,733,616 B2
(45) Date of Patent: May 27, 2014

(54) LOADED SURGICAL STAPLER

(75) Inventors: Pierre Bailly, Caluire (FR); Geneviève Doucet, Villefranche sur Saone (FR); Frèdèric Turquier, Lyons (FR)

(73) Assignee: Sofradim Production (FR)

( * ) Notice: Subject to any disclaimer, the term of this patent is extended or adjusted under 35 U.S.C. 154(b) by 46 days.

(21) Appl. No.: 13/133,414

(22) PCT Filed: Jan. 21, 2010

(86) PCT No.: PCT/IB2010/000290
§ 371 (c)(1),
(2), (4) Date: Aug. 5, 2011

(87) PCT Pub. No.: WO2010/084424
PCT Pub. Date: Jul. 29, 2010

(65) Prior Publication Data
US 2012/0248171 A1    Oct. 4, 2012

(30) Foreign Application Priority Data
Jan. 22, 2009  (FR) ...................................... 09 00273

(51) Int. Cl.
*A61B 17/10*   (2006.01)
*A61B 17/04*   (2006.01)

(52) U.S. Cl.
USPC ..................................................... 227/179.1

(58) Field of Classification Search
None
See application file for complete search history.

(56) References Cited

U.S. PATENT DOCUMENTS

| | | | | |
|---|---|---|---|---|
| 4,610,383 A | * | 9/1986 | Rothfuss et al. | 227/19 |
| 4,627,437 A | * | 12/1986 | Bedi et al. | 606/220 |
| 4,925,082 A | * | 5/1990 | Kim | 227/120 |
| 5,013,316 A | * | 5/1991 | Goble et al. | 606/916 |
| 5,352,229 A | * | 10/1994 | Goble et al. | 606/75 |
| 5,797,714 A | * | 8/1998 | Oddenino | 411/508 |
| 5,941,439 A | * | 8/1999 | Kammerer et al. | 227/67 |
| 6,185,356 B1 | * | 2/2001 | Parker et al. | 385/133 |
| 6,206,897 B1 | * | 3/2001 | Jamiolkowski et al. | 606/157 |
| 6,836,611 B2 | * | 12/2004 | Popovic et al. | 385/146 |
| 7,229,452 B2 | * | 6/2007 | Kayan | 606/142 |
| 7,464,847 B2 | * | 12/2008 | Viola et al. | 227/175.2 |
| 7,481,832 B1 | * | 1/2009 | Meridew et al. | 606/319 |
| 7,670,362 B2 | * | 3/2010 | Zergiebel | 606/311 |
| 7,810,692 B2 | * | 10/2010 | Hall et al. | 227/176.1 |
| 7,828,820 B2 | * | 11/2010 | Stone et al. | 606/232 |
| 7,862,573 B2 | * | 1/2011 | Darois et al. | 606/151 |
| 7,878,749 B2 | * | 2/2011 | Edland | 411/508 |

(Continued)

FOREIGN PATENT DOCUMENTS

| | | | | |
|---|---|---|---|---|
| EP | 714633 A1 | * | 6/1996 | ........ A61B 17/122 |
| EP | 1258437 A | | 11/2002 | |
| EP | 1915954 A | | 4/2008 | |
| WO | WO 03094747 A1 | * | 11/2003 | |

OTHER PUBLICATIONS

International Search Report for PCT/IB2010/000290 date of completion is May 27, 2010 (3 pages).

*Primary Examiner* — Robert Long

(57) ABSTRACT

The present invention relates to a surgical stapler loaded with at least two sets of surgical fasteners (405, 406) of different types that are delivered in a pre-established order. The invention also relates to a surgical kit comprising such a surgical stapler and a textile prosthesis.

15 Claims, 6 Drawing Sheets

(56) References Cited

U.S. PATENT DOCUMENTS

| | | | |
|---|---|---|---|
| 7,918,879 B2* | 4/2011 | Yeung et al. | 606/300 |
| 8,366,741 B2* | 2/2013 | Chin et al. | 606/213 |
| 2005/0240222 A1* | 10/2005 | Shipp | 606/219 |
| 2006/0129154 A1* | 6/2006 | Shipp | 606/73 |
| 2009/0030434 A1* | 1/2009 | Paz et al. | 606/151 |
| 2009/0114701 A1* | 5/2009 | Zemlok et al. | 227/176.1 |
| 2010/0185158 A1* | 7/2010 | Lyon | 604/240 |
| 2010/0198276 A1* | 8/2010 | Krebs et al. | 606/86 R |
| 2010/0292715 A1* | 11/2010 | Nering et al. | 606/151 |
| 2011/0000950 A1* | 1/2011 | Euteneuer et al. | 227/175.1 |
| 2011/0011917 A1* | 1/2011 | Loulmet | 227/181.1 |
| 2011/0087279 A1* | 4/2011 | Shah et al. | 606/219 |

* cited by examiner

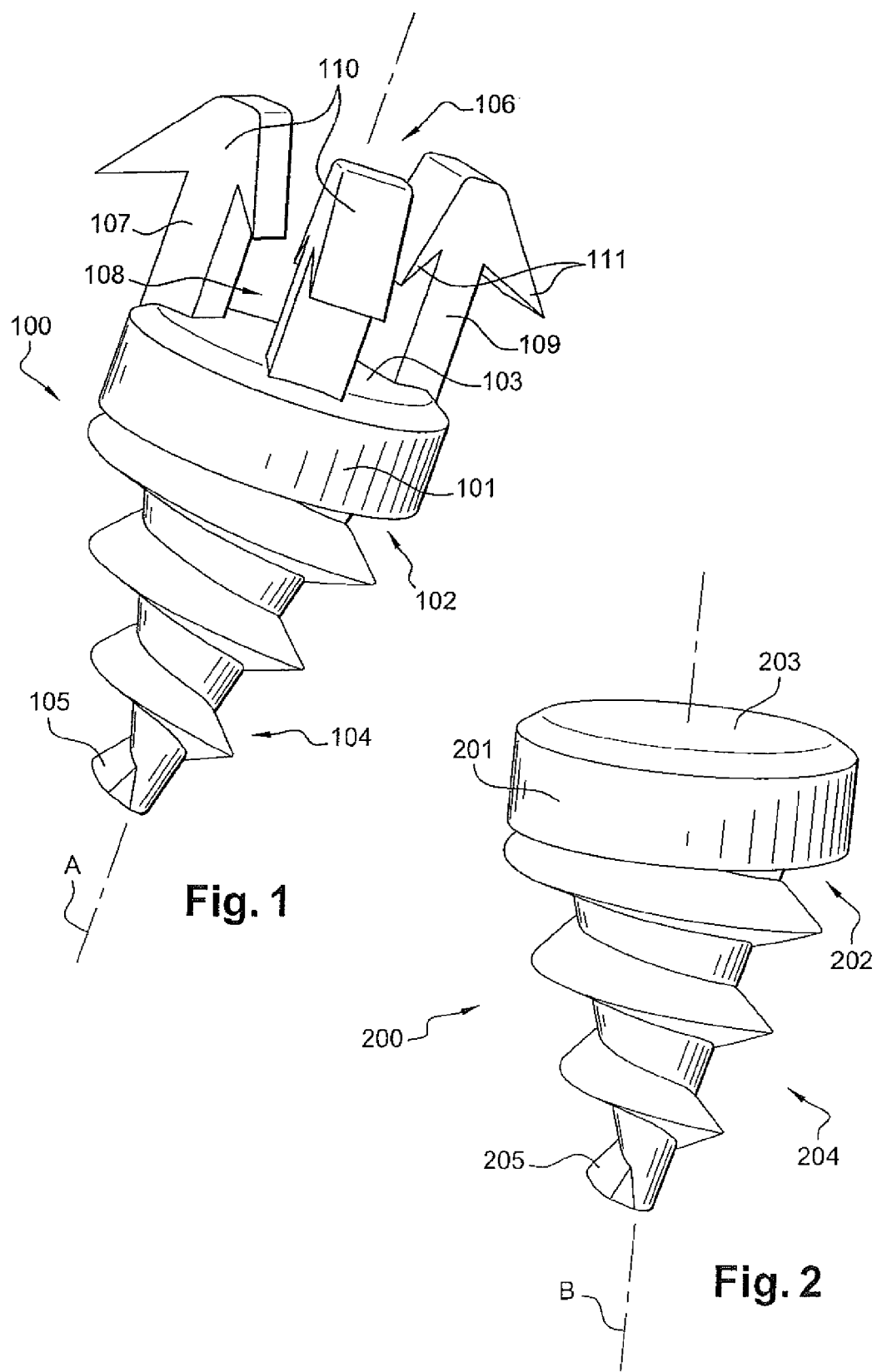

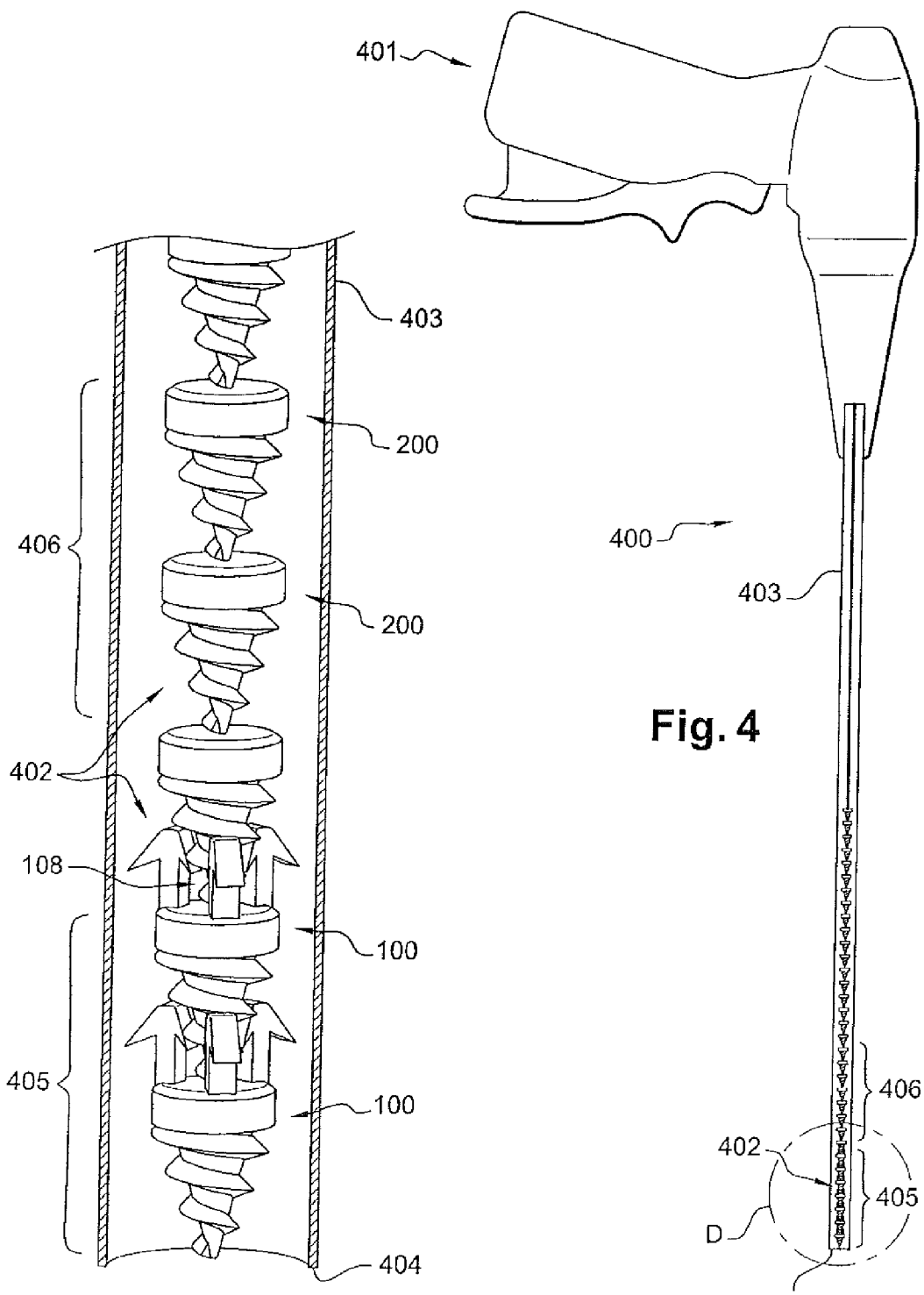

LOADED SURGICAL STAPLER

CROSS-REFERENCE TO RELATED APPLICATIONS

This application is a National Stage Application of PCT/IB2010/000290 under 35 USC §371 (a), which claims priority to French patent application Ser. No. 09/00273, filed Jan. 22, 2009, the disclosures of each of the above-identified applications are hereby incorporated by reference in their entirety.

The present invention relates to a self-fastening surgical staple, a surgical stapler and a method of loading said surgical stapler, which surgical staple, stapler and method can be used in particular for the treatment of hernias.

Prior to the development of surgical endoscopy, the most common way of repairing a hernia defect was to apply tensioned suture threads. However, this type of repair caused the patient pain and, because of the considerable tensioning, posed a considerable risk of tearing of the muscles and aponeuroses by the sutures and/or of recurrence of the hernia.

Nowadays, in order to minimize the risks of recurrence, surgeons frequently implant a textile prosthesis which replaces or reinforces the weakened anatomical tissues without the need to approximate the margins of the damaged tissues. These prostheses are very often placed in position by celioscopy, that is to say by surgical endoscopy of the abdominal cavity. The surgeon uses a needle to introduce carbon dioxide in the region of the navel or below the ribs in order to create a gas cavity spreading apart the wall of the viscera and permitting the manipulation of the instruments that are introduced through small incisions. The prosthesis is introduced with the aid of a trocar and is first of all wound up or folded for this purpose. It then has to be deployed, oriented, centred on the defect and applied against the abdominal wall, in the correct direction if it has a dedicated surface. All of these manoeuvres are carried out with the aid of forceps or standard celioscopy instruments, and the prosthesis is fixed in place by stapling, for example.

The positioning and fixation of a textile prosthesis in intraperitoneal surgery by celioscopy is an operation that an inexperienced surgeon may find difficult to perform. The efficacy of the prosthesis, however, and the ability to minimize the risk of recurrences depend to a large degree on the fixation of said prosthesis. First, the deployment of textile prostheses, which are often flexible, proves difficult, and they therefore have a tendency to form folds on the abdominal wall. The lack of perfect deployment entails a risk of engagement of the peritoneal sac or of the viscera, for example, and increases the possibilities of recurrences or of adherence to the prosthesis. Incorrect deployment can also impede tissue integration of the prosthesis to the peritoneum. It is therefore essential for the surgeon to ensure that no part of the prosthesis is folded and that none of the viscera and no part of the intestine is located between the prosthesis and the abdominal wall.

Document WO 2004/103414 describes a composite surgical tack provided with a head that is covered, with the aid of an adhesive, by a fastening textile to permit temporary positioning of a textile prosthesis. Although a composite surgical tack of this kind may appear satisfactory, it requires several production steps and several different materials. Each of the materials must be efficiently sterilized and may require different sterilization methods. Moreover, the behaviour of such a composite tack in the human body is unpredictable. In particular, its various component elements risk separating for example, or being resorbed at different speeds, or even not degrading. In particular, the adhesives allowing such elements to be assembled are not generally resorbable.

A general aim is always to reduce the sequelae and the trauma that the patients may experience during surgical interventions, while at the same time seeking to facilitate the work of the surgeon and reduce the costs involved. In particular, it is always desirable to simplify the methods of validation of sterilization.

It is an object of the present invention to remedy all or some of the various disadvantages posed by the use of composite surgical tacks of this kind that permit repositioning of a textile prosthesis.

More specifically, the present invention aims to provide a self-fastening surgical staple that permits the positioning and then repositioning of a textile prosthesis while at the same time reducing the trauma inflicted on the patients. A further object of the present invention is to provide self-fastening surgical staples that are obtained in shorter times and with reduced manufacturing costs.

To this end, the present invention proposes a self-fastening surgical staple having a longitudinal axis and comprising a central section with a distal surface and a proximal surface that are perpendicular to the longitudinal axis, said surgical staple further comprising an elongate distal part with screw thread that is able to penetrate into biological tissues and extends distally from said distal surface along the longitudinal axis, and means of removable fixation to a textile, characterized in that the means of removable fixation comprise a plurality of self-fastening stubs forming a harpoon, said self-fastening stubs being distributed on the periphery of said proximal surface and extending proximally from this surface and parallel to the longitudinal axis, each self-fastening stub having the form of an arm that is substantially parallel to the longitudinal axis A and that protrudes from said proximal surface, said arm having at its free end at least a bevelled part directed toward the longitudinal axis.

Within the meaning of the present application, part of an item is defined as distal when this part is situated away from the surgeon's hand during implantation in the tissues, and a proximal part designates a part situated near the surgeon's hand during implantation. Also within the meaning of the present application, distally designates the direction of ejection of the surgical fasteners by a surgical stapler, and proximally designates the direction opposite to distally.

Within the meaning of the present application, "textile" is understood as an arrangement of threads, fibres and/or filaments that is obtained, for example, by knitting, weaving or braiding, or even a nonwoven.

In embodiments of the surgical staple according to the invention, the means of removable fixation are formed integrally with the central section, in such a way that the surgical staple constitutes a one-piece component. For example, the surgical staple according to the invention can be produced economically by moulding.

The self-fastening surgical staple according to the present invention therefore entails reduced production costs since it can be manufactured as a single piece of moulded material. The production of a self-fastening surgical staple according to the invention is therefore simple. The self-fastening surgical staple does not require the assembling of several components and thus makes sterilization easier. This therefore limits the risks of contamination of the patient.

Moreover, as is described further below in the present application, the self-fastening surgical staples according to the invention can be loaded in a conventional surgical stapler, particularly by virtue of the distribution of the self-fastening stubs forming a harpoon that are distributed on the periphery of said proximal surface.

In embodiments of the invention, the proximal surface has a central zone free of said stubs. As will be explained below, said central zone thus free of said stubs makes it possible to optimize the loading of said self-fastening surgical staples according to the invention in a surgical stapler. The central space freed in this way allows the elongate distal part of another surgical fastener to be placed in contact with the central surface of a first self-fastening surgical staple according to the invention. This other surgical fastener can be a surgical staple according to the invention or a conventional surgical fastener.

In embodiments of the invention, the self-fastening surgical staple is made of bioresorbable material. According to the present application, the term "bioresorbable" means the characteristic by which a material is biologically resorbed or degraded by the surrounding biological fluids and tissues and disappears in vivo after a given period of time, which can range, for example, from one day to several months, depending on the chemical nature of the material for example. Among the bioresorbable materials that are suitable for the self-fastening surgical staples according to the invention, mention may be made of lactic acid polymers, glycolic acid polymers, and mixtures thereof. Such a self-fastening surgical staple minimizes the residual sequelae resulting from the intervention: since it is resorbed by the organism, the long-term presence of a foreign body in the patient's body is minimized.

In embodiments of the invention, said self-fastening stubs have a length that is less than or equal to the length of said elongate distal part. As will be explained below, such a length of the self-fastening stubs facilitates the loading of the self-fastening surgical staple according to the invention in a surgical stapler, by allowing the elongate distal part of another surgical fastener to be brought into contact with the central surface.

The present invention also relates to a kit comprising at least one self-fastening surgical fastener according to the invention and at least one patch made of self-fastening textile. Within the meaning of the present invention, self-fastening textile means a textile that is able to attach itself temporarily or removably to another textile, for example by simple pressure, in particular by at least some of the threads of said self-fastening textile interlocking with at least some of the threads of said other textile. In particular, the self-fastening textile of the patches in the kit according to the invention is capable of attaching itself temporarily to a conventional textile prosthesis that comprises meshes and is designed for treatment of hernias.

Thus, in one embodiment of the invention, said patch comprises, on at least one of its faces, a plurality of barbs protruding from said face. Thus, when a conventional textile prosthesis with meshes is pressed onto the face of the patch comprising these barbs, said barbs engage in the meshes of said prosthesis, and the latter becomes attached to the patch, at least temporarily or removably. It suffices to pull the prosthesis and the patch in opposite directions to easily separate them from each other. A self-fastening textile suitable for the kit according to the invention is described in patent application WO 01/81667, for example.

In embodiments of the invention, said patch is made with threads of bioresorbable threads. Preferably, the kit according to the invention comprises a plurality of patches. These patches can each have substantially the shape of a disc measuring 1 cm. A kit according to the present invention can prove useful in carrying out a surgical method according to the present invention, as will be described below.

It is also an object of the present invention to provide a loaded surgical stapler, which in particular makes it possible to reduce the costs of a surgical intervention during which a first set of surgical fasteners, composed of a first type of surgical fasteners that are preferably provided with means of removable fixation, is delivered by said surgical stapler in order to permit preliminary positioning of a textile prosthesis, and during which the fixation of said textile prosthesis is obtained by applying a second set of surgical fasteners.

The present invention proposes a surgical stapler designed to deliver a plurality of fasteners one after another, characterized in that it comprises at least one grip body, at least one mechanism for ejecting said plurality of fasteners, and a tubular ejection barrel in which the surgical fasteners are stored one behind another, the surgical fasteners being delivered distally, at the distal end of said ejection barrel and in that it is loaded with:

at least a first set of fasteners that is composed of surgical fasteners of a first type;
  at least a second set of fasteners that is composed of surgical fasteners of a second type different from said first type;
  said first and second sets of fasteners being arranged according to a pre-established loading plan in such a way as to obtain a predefined order of delivery of the different fasteners.

The order of delivery of the surgical fasteners is directly determined by the loading plan, depending on the type of surgical stapler used to implement the invention.

The surgical stapler according to the invention thus permits the use of a single stapler to effect the preliminary positioning and then the fixation of a textile prosthesis, and it makes it possible to reduce the number of instruments manipulated by the surgeon. Thus, the surgical stapler according to the invention simplifies a surgical procedure and saves the surgeon time, which makes it possible to reduce the costs of an intervention during which it is used. The surgical stapler according to the invention also makes it possible to reduce the risks of confusion that may exist when the surgeon has to use two staplers. Since the number of instruments manipulated by the surgeon is reduced by the use of a surgical stapler according to the invention, the risks of accidental infection are also reduced.

The reduction in the number of instruments that is achieved by using the surgical stapler according to the invention makes the work of the surgeon easier. In particular, the stapler according to the invention eliminates the need to manipulate two conventional staplers, one for delivering the surgical fasteners of the first set of fasteners, the other for delivering the surgical fasteners of the second set of fasteners. The surgical stapler according to the invention also makes it possible to reduce the duration of the surgical interventions by affording the surgeon an optimized procedure.

Surgical staplers are complex devices that are often pre-loaded, disposable and relatively expensive. The surgical stapler according to the invention thus makes it possible to reduce costs.

Finally, the reduction in the number of instruments manipulated makes it possible to limit the risks of accidental contamination of a patient by an instrument that is poorly sterilized, which contamination can be the source of serious complications such as nosocomial infections.

In one embodiment of the invention, the surgical stapler is such that the fasteners of the first set of fasteners are surgical fasteners provided with means of removable fixation to a textile.

In one embodiment of the invention, the surgical stapler is such that the surgical fasteners of said first set of fasteners are arranged in such a way as to be delivered by the surgical stapler before those of said second set of fasteners.

In one embodiment of the invention, the surgical stapler is such that the surgical fasteners of the second set of fasteners are fasteners that are without means of removable fixation to a textile.

In one embodiment of the invention, the surgical stapler is such that the surgical fasteners of the first set of fasteners are self-fastening surgical staples according to the invention as defined above.

In another embodiment of the invention, the surgical stapler is such that the surgical fasteners of the first set of fasteners are fasteners of the kind described in patent application WO 2004/103414.

In one embodiment of the invention, the surgical stapler comprises at least one grip body, at least one mechanism for ejecting the plurality of fasteners, and a tubular ejection barrel in which the surgical fasteners are stored one behind another, the surgical fasteners being delivered distally, at the distal end of said ejection barrel. Thus, the surgical fasteners of the first set of fasteners are preferably arranged in a distal part of the ejection barrel, and the surgical fasteners of the second set of fasteners are preferably arranged in a proximal part of the ejection barrel.

In one embodiment of the invention, the surgical stapler additionally comprises a notification means designed to indicate that one of the first or second set of fasteners has been delivered. Such a notification means can be an audio, visual or tactile means. For example, such a means can be designed in such a way as to be activated after a predefined number of surgical fasteners have been delivered. A notification means suitable for the stapler according to the invention can, for example, comprise a coloured part that appears in a window formed in the body of the stapler after a number of fasteners have been delivered. Another notification means suitable for the stapler according to the invention can, for example, comprise a marker that gradually moves as the fasteners are delivered.

The present invention also relates to a surgical kit comprising at least one surgical stapler according to the invention and a textile prosthesis. The textile prosthesis in the surgical kit according to the invention can be a conventional prosthesis used in the treatment of hernias. The textile prosthesis in the surgical kit according to the invention preferably comprises meshes. The textile prosthesis can be bioresorbable. Textile prostheses suitable for the surgical kit according to the invention are described, for example, in WO 2004/032797, WO03/031709, WO00/42943 or WO99/66860. In one embodiment of the invention, the surgical kit according to the invention additionally comprises a patch made of self-fastening textile, in particular as has already been described above. The surgical kit according to the invention can be used directly by the surgeon for carrying out the surgical method described below.

The present invention also relates to a method of loading a surgical stapler that is able to deliver a plurality of surgical fasteners one after another, characterized in that the method comprises the steps of:

loading the surgical stapler with at least a first set of fasteners that is composed of surgical fasteners of a first type; and loading the same surgical stapler with at least a second set of fasteners that is composed of surgical fasteners of a second type different from said first type;

said first and second sets of fasteners being loaded according to a pre-established loading plan in such a way as to obtain a predefined order of delivery of the different fasteners.

Thus, the loading method according to the invention makes it possible to obtain a surgical stapler according to the invention.

In particular, the composite surgical tacks described in document WO 2004/103414 may be suitable for carrying out the loading method according to the invention so as to obtain a surgical stapler according to the invention: the surgical fasteners of the first set of fasteners are then composite surgical tacks of this kind.

Finally, the present invention relates to a surgical method for positioning a textile prosthesis on a biological wall, which method comprises the steps of:

a) making available a surgical stapler according to the invention;

b) using said surgical stapler to position, on said wall, a first set of fasteners of a first type, said surgical fasteners of said first set (405) being provided with means of removable fixation to a textile;

c) positioning said textile prosthesis on said wall and on said surgical fasteners of said first set (405) that were positioned in step b);

d) pressing the textile prosthesis on said surgical fasteners of the first set of fasteners;

e) adjusting the position of the textile prosthesis on said biological wall by disengaging and re-engaging, as many times as is necessary, said textile prosthesis in and from said means of removable fixation to a textile, of said surgical fasteners of the first set that were positioned in step b);

f) fixing the textile prosthesis, by means of said surgical stapler from step a), with at least a second set of fasteners that is composed of surgical fasteners of a second type different from said first type.

In one embodiment of the invention, the surgical method according to the invention is such that the surgical fasteners of the first set of fasteners are self-fastening surgical staples according to the invention, and such that the fasteners of the second set of fasteners are conventional surgical fasteners that are without means of removable fixation to a textile.

In one embodiment of the invention, the surgical method according to the invention for treatment of a hernia defect is characterized in that the fasteners of the first set of fasteners are arranged on the wall around the defect to be treated, and the prosthesis is engaged and disengaged in and from said fasteners of the first set of fasteners until its correct position with respect to said defect is obtained.

Another aspect of the present invention concerns a surgical method for positioning a textile prosthesis on a biological wall, which method comprises the steps of a) making available a surgical stapler as described above and a plurality of textile patches that each have at least one self-fastening face;

b) positioning one or more textile patches on said wall by pressing each patch with its face opposite the self-fastening face against said wall, and fixing said patches to said wall with the aid of the first set of fasteners of a first type;

c) positioning said textile prosthesis on said wall and on said textile patches;

d) pressing the textile prosthesis on said patches;

e) adjusting the position of the textile prosthesis on said biological wall by disengaging and re-engaging, as many times as is necessary, said textile prosthesis in and from the self-fastening surfaces of said patches;

f) fixing the textile prosthesis, by means of said surgical stapler from step a), with at least a second set of fasteners that is composed of surgical fasteners of a second type different from said first type.

The invention will be readily understood from the following description given as a non-limiting example and by reference to the attached drawing, in which:

FIG. 1 is a perspective view of a self-fastening surgical staple according to the invention;

FIG. 2 is a perspective view of a conventional surgical fastener without means of removable fixation to a textile;

FIG. 4 shows a side view of a surgical stapler according to the invention, said surgical stapler being loaded with surgical fasteners of two different types;

FIG. 5 is a sectional view, on a larger scale, of the detail of zone D from FIG. 4;

Figure 3:
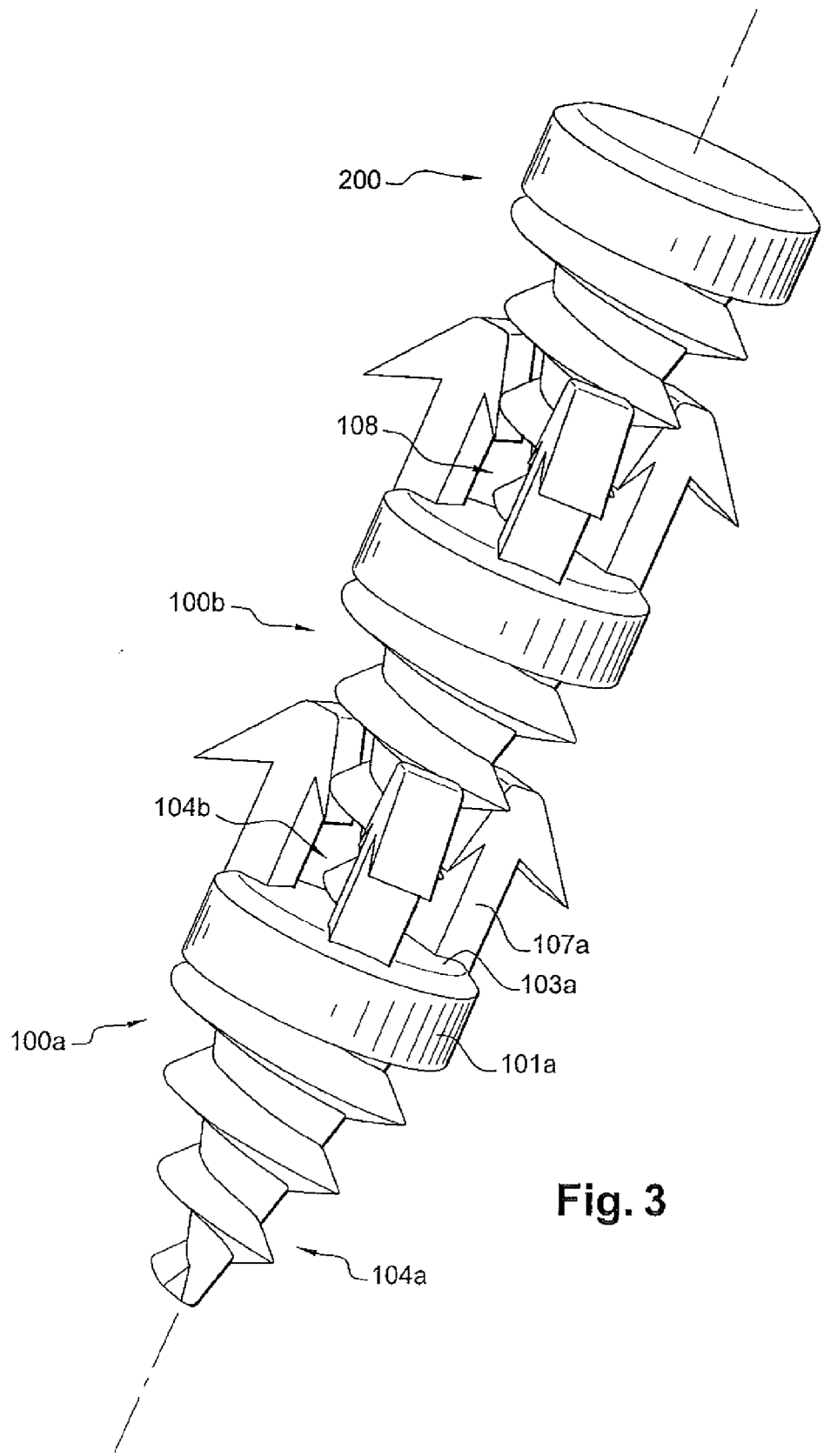
FIG. 3 shows a perspective view of a stack of three surgical fasteners comprising two self-fastening surgical staples according to the invention and a conventional surgical fastener.

In FIG. 1, a self-fastening surgical staple 100 according to the invention is shown in perspective. Said self-fastening surgical staple 100 has a longitudinal axis A and comprises a central section 101 with a distal surface 102, circular in the example shown, and a proximal surface 103, circular in the example shown, which surfaces are perpendicular to the longitudinal axis A. Said surgical staple 100 additionally comprises an elongate distal part 104 with screw thread 105 that is able to penetrate into biological tissues, particularly in order to provide fixation to said tissues, and extends distally from said distal surface 102 along the longitudinal axis A. Said surgical staple 100 further comprises means 106 of removable fixation to a textile. Said means 106 of removable fixation comprise a plurality of self-fastening stubs 107 forming a harpoon, said stubs 107 being three in number in the example shown and being distributed on the periphery of said proximal surface 103 and extending proximally from this surface and parallel to the longitudinal axis A.

These self-fastening stubs 107 have, for example, the form of an arm 109 that is substantially parallel to the longitudinal axis A and that protrudes from said proximal surface 103. At its free end, each arm 109 is provided with an arrow-shaped anchoring head 110 pointing in the direction away from the proximal surface 103, said anchoring head 110 thus having two mutually opposite bevelled parts 111 relative to said arm 109. As a consequence, for each arm 109, at least one bevelled part 111 is directed towards the central longitudinal axis A. Such an embodiment allows a good fixation of a textile to the self-fastening stubs 107.

In the example shown, the means of removable fixation, namely the stubs 107, are formed integrally with the central section 101, and the self-fastening surgical staple 100 is formed from a one-piece component, obtained by moulding for example.

As will be seen from FIG. 1, the proximal surface 103 has a central zone 108 free of said stubs 107.

According to one embodiment of the invention, the surgical staple 100 is made of resorbable material. For example, the surgical staple can be made of polylactic acid or polyglycolic acid. This makes it possible to minimize the sequelae inflicted on the body in which the staple is implanted. When a textile prosthesis, pre-positioned with the aid of a set of surgical staples 100, has been fixed with the aid of conventional surgical fasteners according to a surgical method of the invention, said surgical staple 100 is no longer necessary and can therefore be resorbed.

In an embodiment not shown, the self-fastening surgical staple 100 comprises screwing means. These means allow said surgical staple to be screwed into biological tissues and can comprise, for example, slits formed in the proximal surface 103.

In FIG. 2, a conventional surgical fastener 200 is shown in perspective. Said conventional surgical fastener 200 has a longitudinal axis B and comprises, for example, a central section 201 with a distal surface 202 and a proximal surface 203 that are perpendicular to the longitudinal axis B. Said conventional surgical fastener 200 additionally comprises an elongate distal part 204 with screw thread 205 that is able to penetrate into biological tissues, in order to provide fixation to said tissues, and extends distally from said distal surface 202 along the longitudinal axis B. Such fasteners are described in patent application US 2007/0038220, for example.

As is shown in FIG. 3, surgical fasteners 100a, 100b according to the invention can be stacked in such a way that their respective longitudinal axes coincide. Thus, according to one embodiment of the invention, and in order to make such stacks easier and more compact, said stubs 107a of a self-fastening surgical staple 100a according to the invention have a length that is shorter than the length of said elongate distal part 104a. This makes it possible, in particular, to place the end of the elongate distal part 104b of another surgical staple 100b in the space freed by the central zone 108 without stubs 107.

In stacks of surgical fasteners containing self-fastening surgical staples 100a, 100b according to the invention, at least one conventional surgical fastener 200, without means of removable fixation as shown in FIG. 2, can be placed in the same way as the surgical staple 100b in order to form a mixed stack.

In one embodiment of the invention, shown in FIG. 3, the elongate distal part 104b of said staple 100b is in contact with the proximal surface 103a of the central section 101a of said surgical staple 100a in order to form a compact mixed stack. In another alternative embodiment not shown, the elongate distal end 104b is not in contact with the proximal surface 103a, but with part of the means 107a of removable fixation.

Advantageously, a compact mixed stack does not take up any more space than a first stack of a defined number of self-fastening surgical staples 100 or than a second stack composed of the same defined number of conventional surgical fasteners 200; in particular, the three stacks occupy the same length.

Thus, the self-fastening surgical staples 100 according to the invention are of particular interest when loading them into a conventional stapler within which said surgical staples are stored in the form of a stack as described above; such a stapler is described, for example, in the patent applications US 2005/0240222 and US 2006/129154. Such a surgical stapler can be loaded equally with conventional surgical fasteners 200 or with self-fastening surgical staples 100 according to the invention or with an alternating sequence of the two types of surgical fasteners, in a predefined order, in accordance with the loading method of the invention.

Advantageously, the particular shape of a self-fastening surgical staple 100 according to the invention can be adapted such that the central section 101 and/or the elongate distal part 104 have substantially the same shapes and the same dimensions as the central section 201 and/or the elongate distal part 204, respectively, of a conventional surgical fastener 200; the self-fastening surgical staples 100 according to the invention can then be loaded into a surgical stapler designed for conventional surgical fasteners 200.

FIG. 4 shows a surgical stapler 400 loaded according to the invention. Such a surgical stapler 400 conventionally comprises, for example, a grip body 401, allowing the surgeon to manipulate said surgical stapler 400, and an ejection system or mechanism for triggering the delivery of surgical fasteners 402, the latter being stored within a tubular ejection barrel 403. The surgical stapler 400 according to the invention is loaded with surgical fasteners 402 chosen from at least two different types of fastener and constituting a first set of fasteners 405 of a first type and a second set of fasteners 406 of a second type. The surgical fasteners 402 are delivered one after another at the end 404 of the ejection barrel 403. In one embodiment of the invention, as shown in FIGS. 4 and 5, said surgical fasteners 402 are stored in the ejection barrel to form a stack, as has been described above for FIGS. 3, 4 and 5. Such a stack comprises at least two different types of fasteners, which respectively constitute a first set of fasteners 405 and a second set of fasteners 406.

When the surgical fasteners are stored in the ejection barrel 403, the order of delivery of the surgical fasteners 402 is determined by their proximity to the distal end 404 of the ejection barrel 403: the surgical fasteners 402 closest to the distal end are delivered before the surgical fasteners 402 farther from said distal end 404.

A surgical stapler suitable for the invention is a surgical stapler in which the surgical fasteners are stored in a pre-established order. In an alternative manner not shown here, they can be stored in a magazine of said surgical stapler, such as a cylinder or a cartridge. In this case, the surgical stapler that is suitable comprises guide means for bringing said surgical fasteners into an ejection barrel in an order that depends solely on the arrangement of said fasteners in said magazine and on said guide means. Thus, for example, when the magazine comprises a cylinder, said guide means ensure rotation of the cylinder in a defined direction in order to bring one or more of the surgical fasteners contained in the cylinder into line with the ejection barrel, in an order that depends on their positions in said cylinder.

In one embodiment not shown, the surgical stapler according to the invention additionally comprises a notification means for indicating that one of the first set or second set of fasteners has been delivered. Such a notification means can comprise, for example, a coloured part that appears in a window formed in the body of the stapler after a number of fasteners have been delivered. Alternatively, such a notification means can also comprise a marker that moves gradually as the fasteners are delivered.

FIG. 5 shows an enlarged view of the zone marked D in FIG. 4. In this figure, it is possible to distinguish a first set of fasteners and a second set of fasteners, the two sets being composed of distinct types of fasteners. In FIG. 5, for example, a first set of fasteners is composed of self-fastening surgical staples 100 according to the invention, and the second set of fasteners is composed of conventional surgical fasteners 200. Only a small number of surgical fasteners of each type have been shown in FIG. 5. It is of course possible to adjust the numbers of surgical fasteners of the first set of fasteners 405 or of the second set of fasteners 406. The surgical fasteners 402 are arranged in the surgical stapler 400 according to a pre-established loading plan according to which the surgical staples 100 of the first set of fasteners 405 are delivered before the conventional surgical fasteners 200 of the second set of fasteners 406. Thus, in FIG. 5, the surgical fasteners of the first set of fasteners 405 are arranged in a distal part of the ejection barrel 403, and the surgical fasteners of the second set of fasteners 406 are arranged in a proximal part of the ejection barrel 403.

For example, the first set of fasteners 405 can be composed of five or six self-fastening surgical staples 100 according to the invention, and the second set of fasteners 406 can be composed of fourteen or fifteen conventional surgical fasteners 200. To obtain a surgical stapler according to the invention that is especially suitable for fitting a textile prosthesis, a conventional surgical stapler 400 can be chosen that is loaded with the five or six self-fastening surgical staples 100 according to the invention and with the fourteen or fifteen conventional surgical fasteners 200. The loading plan is such that said self-fastening surgical staples 100 according to the invention can be delivered before the conventional surgical fasteners 200 during normal use of said surgical stapler 400. The surgical staples 100 constituting the first set of surgical fasteners 405 are delivered before the surgical fasteners 200 of the second set of fasteners 406.

Such a surgical stapler according to the invention can be particularly useful in implementing the surgical method described below and illustrated by FIGS. 6a to 6e. The use of such a surgical stapler according to the invention avoids the surgeon having to use two separate staplers. It therefore makes it possible to reduce costs, to make the work of the surgeon easier and to minimize the risks of accidental contamination, by reducing the number of instruments used during the intervention.

FIGS. 6a to 6e are schematic views representing different steps in a surgical intervention using the surgical stapler 400 according to the invention and self-fastening surgical staples 100 according to the invention.

Figure 6A:
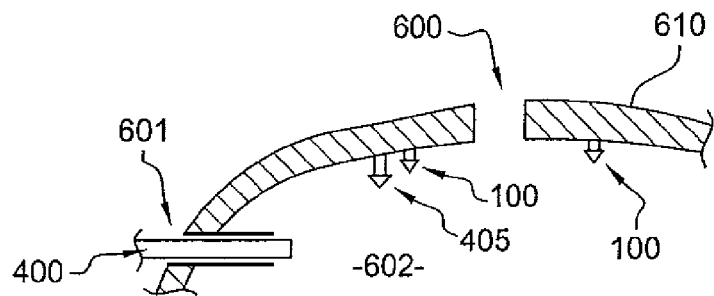
FIGS. 6a to 6e show schematic views of different steps involved in a surgical intervention using the surgical stapler according to the invention and self-fastening surgical staples according to the invention.

FIG. 6a shows a defect 600 in the abdominal wall 610 to be repaired by celioscopy. A trocar 601 is introduced into the abdominal cavity 602 through an incision made on the side of the patient's abdomen. A first set of fasteners 405, composed for example of self-fastening surgical staples 100 according to the invention, is positioned around the defect 600 in the abdominal wall 610 with the aid of a surgical stapler 400 according to the invention introduced at the site of implantation by way of the trocar 601. These surgical staples 100 are the first surgical fasteners 402 delivered by the surgical stapler 400 shown for example in FIGS. 4 and 5.

Figure 6B:
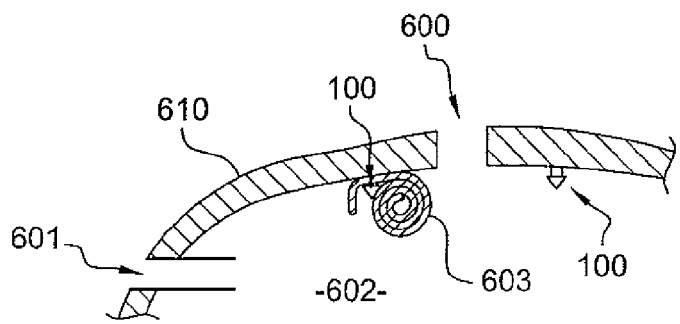

Once the required number of self-fastening surgical staples 100 have been placed around the defect 600 that is to be repaired, a textile prosthesis 603 designed to reinforce the abdominal wall 610 is introduced with the aid of the trocar 601 and in a rolled-up form, as is shown in FIG. 6b. The textile prosthesis preferably has a mesh structure. This prosthesis 603 is placed in contact on one or more self-fastening surgical staples 100 according to the invention. Said textile prosthesis 603 is fixed by the textile fibres of said prosthesis 603 engaging with the means of removable fixation 106, via said self-fastening stubs 107, of said self-fastening surgical staples 100. By virtue of the plurality of the self-fastening stubs 107 of the surgical staples 100 according to the invention, of which the anchoring heads 110 forming a harpoon are capable of engaging with and easily disengaging from the threads of the textile of the prosthesis 603, the latter can be repositioned as many times as is desired by the surgeon.

Figure 6C:
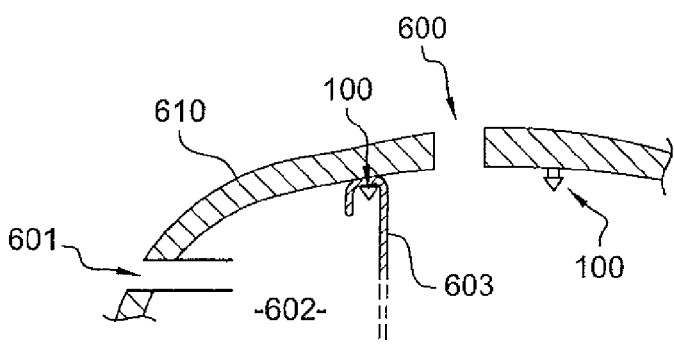

In FIG. 6c, the textile prosthesis 603 is unrolled and suspended in the abdominal cavity 602 by one or more self-fastening surgical staples 100 according to the invention.

Figure 6D:
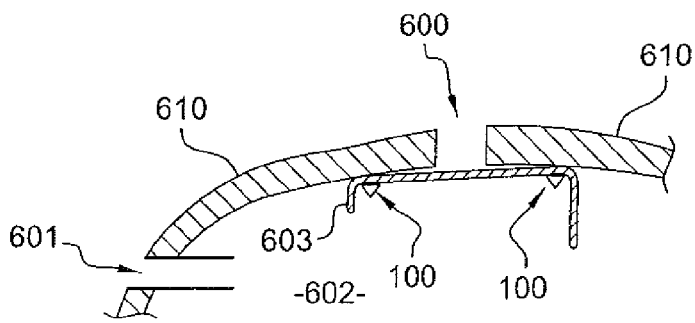

In FIG. 6d, the textile prosthesis 603 has been deployed on the defect 600 of the abdominal wall 610. The deployment has brought said prosthesis 603 into contact with all of the self-fastening surgical staples 100 of said first set of fasteners 405 that have been positioned on the abdominal wall 610 during the first step of the surgical intervention described above: the self-fastening surgical staples 100 then ensure the removable fixation of said prosthesis 603 by engagement of the textile with the means of removable fixation 106, in particular the self-fastening stubs 107 of the surgical staple 100 according to the invention. The textile prosthesis 603 can be repositioned by the surgeon by simply disengaging and re-engaging said means 106 of removable fixation. The surgeon can thus be assured of suitable centring and deployment of the prosthesis 603 around the defect 600 of the abdominal wall 610.

Figure 6E:
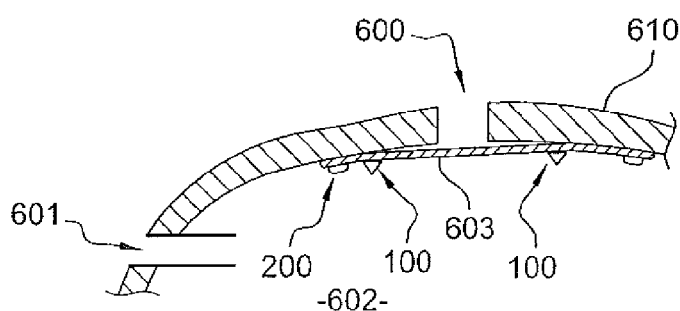

In FIG. 6e, a second set of fasteners 406, formed for example by conventional surgical fasteners 200, have been positioned so as to fix said textile prosthesis 603. These fasteners have been delivered by the same surgical stapler 400 according to the invention that has allowed delivery of the first self-fastening surgical staples 100. Without the surgical stapler 400 according to the invention, the surgeon would have to use a second surgical stapler loaded with conventional surgical fasteners 200. Thus, the surgeon can be assured of a correct positioning of the textile prosthesis 603 and of its fixation by simple use of a single surgical stapler according to the invention.

The self-fastening surgical staples 100 according to the invention are advantageously made of a resorbable material. The reason for this is that once the fixation of the prosthesis 603 has been ensured by the conventional surgical staples 200, the self-fastening surgical staples 100 are no longer necessary.

Although the surgical stapler according to the invention or the above method are described here with a first set of fasteners 405 composed of self-fastening surgical staples 100 according to the invention, it will be appreciated that fasteners such as those described in patent application WO 2004/103414, for example, can also be used to carry out the surgical method according to the invention. Thus, such fasteners could be used in place of the self-fastening surgical staples 100 in the surgical method described above in order to form the first set of fasteners 405.

FIGS. 7a to 7f illustrate a variant of the surgical method according to the invention in which a plurality of patches 710 of self-fastening textile have been pre-positioned around the defect 600 to be repaired, said patches 710 comprising, on at least one of their faces, barbs 720 designed to hook into the meshes of the prosthesis 603. Such patches 710 can be obtained from a self-fastening textile as described in WO 01/81667, for example. Such patches 710 can, for example, be shaped substantially as a disc measuring about 1 cm in diameter. Such patches 710 can be made of bioresorbable material.

Figure 7A:
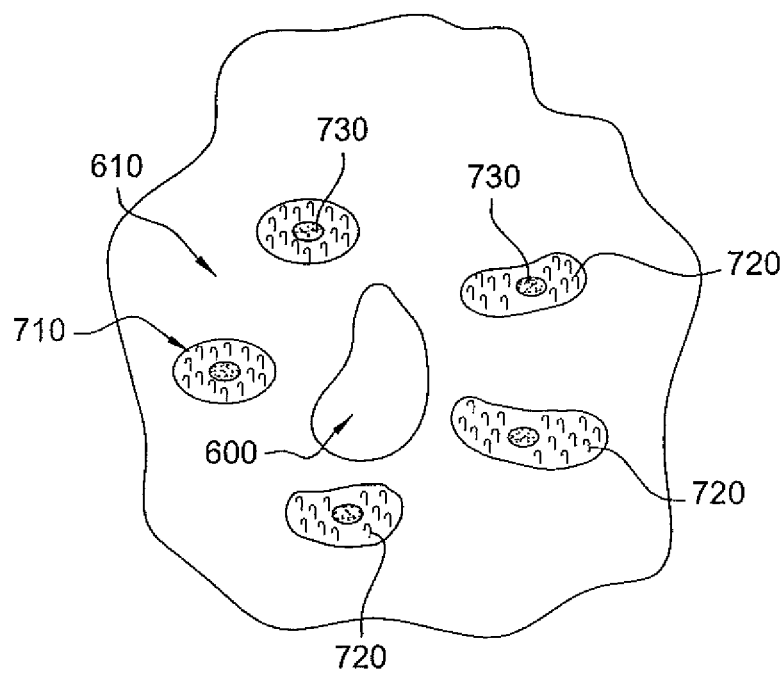
FIGS. 7a to 7f show schematic views of the different steps in a variant of the surgical method according to the invention.
Figure 7B:
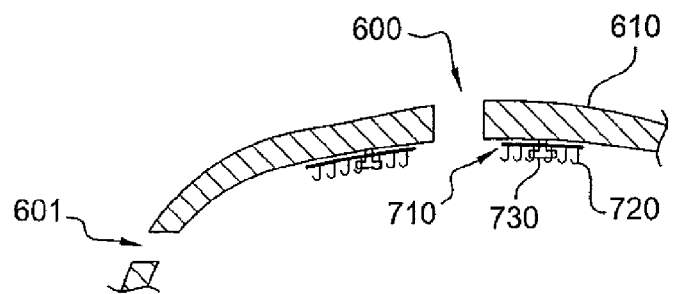
Figure 7C:
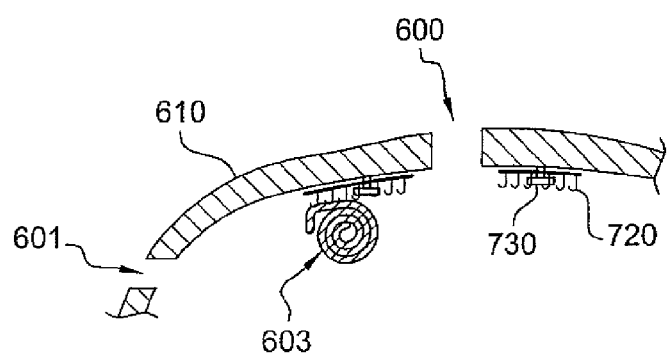
Figure 7D:
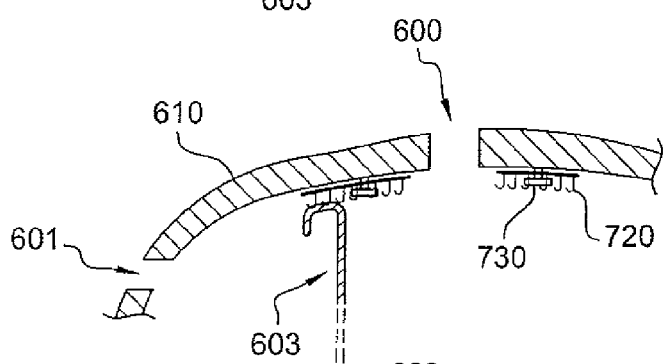
Figure 7E:
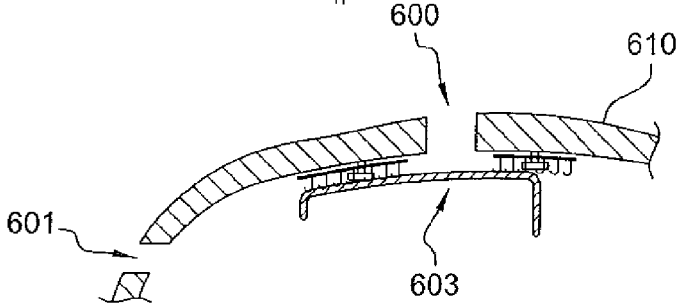
Figure 7F:
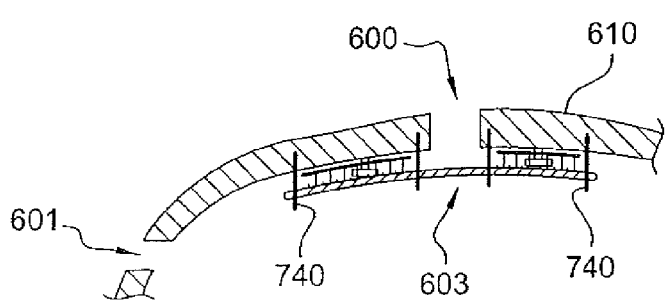

As is shown in FIG. 7a, which is a bottom view, and in FIG. 7b, which is a sectional view, the patches 710 are positioned around the defect 600 by pressing each patch 710 with its face opposite the self-fastening face against said wall 610 and by fixing these patches 710 with the aid of a surgical stapler 400 according to the invention, by delivering a first set of surgical fasteners 730. These surgical fasteners 730 can be self-fastening surgical staples according to the invention. Alternatively, in this step it is possible to use conventional staples 200 such as those described above, or fasteners such as those described in WO 2004/103414.

Once the patches 710 have been fixed, the same procedure as described above is followed in order to position the textile prosthesis 603 correctly around the defect 600 by pressing said textile prosthesis 603 on said patches 710, then by adjusting it, by disengagement and re-engagement, as many times as is necessary, to and from the self-fastening faces of said patches 710, as is described in FIGS. 7b to 7e. The textile prosthesis 603 is then fixed definitively by means of the surgical stapler 400 from the first step, using at least a second set of fasteners, composed for example of surgical fasteners 740 of a second type different from the first type.

The present invention proposes a self-fastening surgical staple 100 that is simple to produce and to use. Such self-fastening surgical staples 100 can be used in combination with another type of surgical fastener in order to load a surgical stapler 400 in such a way as to obtain a surgical stapler loaded according to the invention. This permits the use of a simplified surgical method that reduces the number of manoeuvres by the surgeon. The surgical stapler according to the invention reduces the costs of the surgical intervention by avoiding the use of two staplers, which also minimizes the risks of contamination of the patient.

The invention claimed is:

1. A surgical stapler designed to deliver a plurality of fasteners one after another, the surgical stapler comprises at least one grip body, at least one mechanism for ejecting the plurality of fasteners, and a tubular ejection barrel in which the plurality of fasteners are stored one behind another, the plurality of fasteners being delivered distally, at a distal end of the tubular ejection barrel, the plurality of fasteners including: at least a first set of fasteners including a longitudinal axis, a central section with a proximal surface and a distal surface, an elongate distal part that is able to penetrate into biological tissue and extends distally from the distal surface of the central section and a plurality of self-fastening stubs extending proximally from the proximal surface of the central section; and, at least a second set of fasteners without a plurality of self-fastening stubs.

2. The surgical stapler according to claim 1, wherein the distal surface of the central section is perpendicular to the longitudinal axis.

3. The surgical stapler according to claim 1, wherein the surgical fasteners of the first set of fasteners are arranged in such a way as to be delivered by the surgical stapler before the surgical fasteners of the second set of fasteners.

4. The surgical stapler according to claim 2, wherein elongate distal part further comprises a screw thread.

5. The surgical stapler according to claim 1, wherein the plurality of self-fastening stubs form a harpoon.

6. The surgical stapler according to claim 1, wherein the first set of fasteners are arranged in a distal part of the ejection barrel, and the second set of fasteners are arranged in a proximal part of the ejection barrel.

7. A surgical kit comprising at least one surgical stapler according to claim 1, and a textile prosthesis.

8. A surgical kit according to claim 7, wherein the textile prosthesis comprises at least one self-fastening textile.

9. A method of loading a surgical stapler according to claim 1, that is able to deliver a plurality of surgical fasteners one after another, characterized in that the method comprises the steps of:

loading the surgical stapler with at least a first set of fasteners that is composed of surgical fasteners of a first type; and loading the surgical stapler with at least a second set of fasteners that is composed of surgical fasteners of a second type different from the first type; said first and second sets of fasteners being loaded according to a pre-established loading plan in such a way as to obtain a predefined order of delivery of the different fasteners.

10. The surgical stapler according to claim 1 wherein the plurality of self-fastening stubs are distributed on a periphery of the proximal surface of the central section.

11. The surgical stapler according to claim 10 wherein the proximal surface comprises a central zone free of the plurality of self-fastening stubs.

12. The surgical stapler according to claim 1 wherein the plurality of self-fastening stubs each include an arm that extends substantially parallel to the longitudinal axis and a free end including an anchoring head.

13. The surgical stapler according to claim 12 wherein the anchoring head comprises at least one bevelled part directed towards a central longitudinal axis.

14. The surgical stapler according to claim 12 wherein the anchoring head comprises two mutually opposite bevelled parts relative to the arm.

15. The surgical stapler according to claim 1 wherein the proximal surface of the central section is perpendicular to the longitudinal axis.

* * * * *